(12) United States Patent
Libbus et al.

(10) Patent No.: US 8,923,962 B2
(45) Date of Patent: *Dec. 30, 2014

(54) SAFETY CONTROL SYSTEM FOR IMPLANTABLE NEURAL STIMULATOR

(71) Applicant: Cardiac Pacemakers, Inc., St. Paul, MN (US)

(72) Inventors: Imad Libbus, St. Paul, MN (US); Andrew P. Kramer, Marine on St. Croix, MN (US); William J. Linder, Golden Valley, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/758,696

(22) Filed: Feb. 4, 2013

(65) Prior Publication Data

US 2013/0150927 A1    Jun. 13, 2013

Related U.S. Application Data

(60) Continuation of application No. 13/282,325, filed on Oct. 26, 2011, now Pat. No. 8,391,972, which is a continuation of application No. 12/469,020, filed on May 20, 2009, now Pat. No. 8,050,753, which is a division of application No. 11/135,883, filed on May 24, 2005, now Pat. No. 7,551,958.

(51) Int. Cl.
*A61N 1/00* (2006.01)
*A61N 1/36* (2006.01)
*A61N 1/37* (2006.01)

(52) U.S. Cl.
CPC ........ *A61N 1/36142* (2013.01); *A61N 1/36114* (2013.01); *A61N 1/37* (2013.01)
USPC .................................................. 607/2; 607/63

(58) Field of Classification Search
CPC ........................ A61N 1/36142; A61N 1/36146
See application file for complete search history.

(56) References Cited

U.S. PATENT DOCUMENTS 5,222,492 A    6/1993   Morgan et al.
5,222,494 A *  6/1993   Baker, Jr. ...................... 607/118
(Continued)

FOREIGN PATENT DOCUMENTS

JP    6-210011 A    8/1994
JP    7-506525 A    7/1995
(Continued)

OTHER PUBLICATIONS

"U.S. Appl. No. 11/135,883, Advisory Action mailed Dec. 10, 2008,", 3 pgs.

(Continued)

*Primary Examiner* — Eric D. Bertram
(74) *Attorney, Agent, or Firm* — Schwegman Lundberg & Woessner, P.A.

(57) ABSTRACT

A neural stimulation system includes a safety control system that prevents delivery of neural stimulation pulses from causing potentially harmful effects. The neural stimulation pulses are delivered to one or more nerves to control the physiological functions regulated by the one or more nerves. Examples of such harmful effects include unintended effects in physiological functions associated with autonomic neural stimulation and nerve injuries caused by excessive delivery of the neural stimulation pulses.

20 Claims, 9 Drawing Sheets

(56) References Cited

U.S. PATENT DOCUMENTS

| | | | |
|---|---|---|---|
| 5,372,607 A | 12/1994 | Stone et al. | |
| 5,674,254 A | 10/1997 | van Krieken | |
| 5,916,239 A | 6/1999 | Geddes et al. | |
| 6,463,328 B1 | 10/2002 | John | |
| 6,922,589 B2 | 7/2005 | Stahmann et al. | |
| 7,551,958 B2 * | 6/2009 | Libbus et al. | 607/2 |
| 8,050,753 B2 * | 11/2011 | Libbus et al. | 607/2 |
| 8,391,972 B2 * | 3/2013 | Libbus et al. | 607/2 |
| 2003/0176894 A1 * | 9/2003 | Stahmann et al. | 607/9 |
| 2004/0111041 A1 | 6/2004 | Ni et al. | |
| 2004/0199210 A1 | 10/2004 | Shelchuk | |
| 2005/0149127 A1 | 7/2005 | Libbus | |
| 2006/0135998 A1 | 6/2006 | Libbus et al. | |
| 2006/0161209 A1 | 7/2006 | Pastore et al. | |
| 2006/0271108 A1 | 11/2006 | Libbus et al. | |
| 2009/0228079 A1 | 9/2009 | Libbus | |
| 2012/0041519 A1 | 2/2012 | Libbus et al. | |

FOREIGN PATENT DOCUMENTS

| | | |
|---|---|---|
| JP | H11505165 A | 5/1999 |
| JP | 2004508871 A | 3/2004 |
| WO | WO-0224063 A2 | 3/2002 |
| WO | WO-0245791 A2 | 6/2002 |
| WO | WO-2006127366 A1 | 11/2006 |

OTHER PUBLICATIONS

"U.S. Appl. No. 11/135,883, Final Office Action mailed Sep. 16, 2008", 7 pgs.

"U.S. Appl. No. 11/135,883, Non Final Office Action mailed Feb. 5, 2008", 7 pgs.

"U.S. Appl. No. 11/135,883, Notice of Allowance mailed Feb. 17, 2009", 4 pgs.

"U.S. Appl. No. 11/135,883, Response filed Jan. 16, 2009 to Final Office Action mailed Sep. 16, 2008 and Advisory Action mailed Dec. 10, 2008", 9 pgs.

"U.S. Appl. No. 11/135,883, Response filed May 29, 2008 to Non Final Office Action mailed Feb. 5, 2008", 9 pgs.

"U.S. Appl. No. 11/135,883, Response filed Nov. 17, 2008 to Final Office Action mailed Sep. 16, 2008", 8 pgs.

"U.S. Appl. No. 12/469,020, Non Final Office Action mailed Feb. 4, 2011", 9 pgs.

"U.S. Appl. No. 12/469,020, Notice of Allowance mailed Jul. 22, 2011", 5 pgs.

"U.S. Appl. No. 12/469,020, Response filed May 3, 2011 to Non Final Office Action mailed Feb. 4, 2011", 10 pgs.

"U.S. Appl. No. 13/282,325, Response filed Oct. 11, 2012 to Non Final Office Action mailed Jul. 27, 2012", 7 pgs.

"U.S. Appl. No. 13/282,325, Non Final Office Action mailed Jul. 27, 2012", 6 pgs.

"U.S. Appl. No. 13/282,325, Notice of Allowance mailed Oct. 30, 2012", 5 pgs.

"U.S. Appl. No. 13/282,325, Restriction Requirement mailed Jun. 14, 2012", 8 pgs.

"U.S. Appl. No. 13/282,325, Response to Restriction Requirement filed Jul. 16, 2012", 8 pgs.

"European Application Serial No. 06770521.0, Communication mailed Mar. 5, 2008", 2 pgs.

"European Application Serial No. 06770521.0, Office Action mailed Apr. 13, 2010", 5 pgs.

"European Application Serial No. 06770521.0, Office Action Response Filed Oct. 14, 2010", 8 pgs.

"European Application Serial No. 06770521.0, Response filed Apr. 9, 2008 to Communication mailed Mar. 5, 2008", 7 pgs.

"European Divisional Application Serial No. 11166436.3, Response filed Mar. 5, 2012 to EP Search Report dated Aug. 5, 2011", 4 pgs.

"European Patent Application No. 11166436.3, European Search Report mailed Aug. 5, 2011", 11 pgs.

"European Serial No. Application No. 06770521.0, Communication mailed May 8, 2009", 2 pgs.

"European Serial No. Application No. 06770521.0, Response filed Sep. 11, 2009 to Communication mailed May 8, 2009", 3 pgs.

"International Application Serial No. PCT/US2006/019142, International Search Report and Written Opinion mailed Oct. 20, 2006", 13 pgs.

"Japanese Application Serial No. 2008-513543, Non Final Office Action dated Mar. 12, 2012", w/ English Translation, 7 pgs.

"Japanese Application Serial No. 2008-513543, Office Action mailed Nov. 8, 2011", (w/ partial English Translation), 4 pgs.

"Japanese Application Serial No. 2008-513543, Office Action Response filed Feb. 14, 2012", English Translation Only, 5 pgs.

"Japanese Application Serial No. 2008-513543, Response filed Jun. 8, 2012 to Office Action mailed Mar. 12, 2012", English Claims with response, 7 pgs.

"Japanese Application Serial No. 2008-513543, Voluntary Amendment filed May 18, 2009", (w/ English Translation of Amended Claims), 12 pgs.

Brockway, M., "Controlled Titration of Neurostimulation Therapy", U.S. Appl. No. 11/468,143, filed Aug. 29, 2006, 26 pgs.

Haefner, Paul A, et al., "Method and Apparatus for Neural Stimulation With Respiratory Feedback", U.S. Appl. No. 11/468,595, filed Aug. 30, 2006, 51 pgs.

Lee, Kent, et al., "Method and Apparatus for Controlling Neural Stimulation During Disordered Breathing", U.S. Appl. No. 11/468,603, filed Aug. 30, 2006, 48 pgs.

\* cited by examiner

SAFETY CONTROL SYSTEM FOR IMPLANTABLE NEURAL STIMULATOR

CLAIM OF PRIORITY

This application is a continuation of U.S. application Ser. No. 13/282,325, filed on Oct. 26, 2011, now issued as U.S. Pat. No. 8,391,972, which is a continuation of U.S. application Ser. No. 12/469,020, filed on May 20, 2009, now issued as U.S. Pat. No. 8,050,753, which is a divisional of U.S. application Ser. No. 11/135,883, filed May 24, 2005, now issued as U.S. Pat. No. 7,551,958, each of which is hereby incorporated by reference in its entirety.

TECHNICAL FIELD

This document generally relates to medical devices and particularly to a neural stimulator including a safety control system to ensure safety of neural stimulation.

BACKGROUND

Neural stimulation is applied to treat various pathological conditions. Controlled delivery of electrical stimulation pulses to a nerve restores or modulates the activity of that nerve, thereby restoring the functions of that nerve and/or regulating the functions of the tissue or organ innervated by that nerve. One specific example of neural stimulation is to regulate cardiac functions and hemodynamic performance by delivering electrical stimulation pulses to portions of the autonomic nervous system. The heart is innervated with sympathetic and parasympathetic nerves. Activities in these nerves, including artificially applied electrical stimuli, modulate cardiac functions and hemodynamic performance. Direct electrical stimulation of parasympathetic nerves can activate the baroreflex, inducing a reduction of sympathetic nerve activity and reducing blood pressure by decreasing vascular resistance. Sympathetic inhibition, as well as parasympathetic activation, has been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

While a patient with neurological and/or other disorders may potentially benefit from neural stimulation, improper delivery of electrical energy to the nervous system may cause nerve injury and unintended effects in various physiological functions. Therefore, there is a need to protect the patient from potentially harmful side effects associated with neural stimulation.

SUMMARY

A neural stimulation system includes a safety control system that prevents delivery of neural stimulation pulses from causing potentially harmful effects. The neural stimulation pulses are delivered to one or more nerves to control the physiological functions regulated by the one or more nerves.

In one embodiment, a neural stimulation system includes a stimulation output circuit, a stimulation controller, and a safety controller. The stimulation output circuit includes at least one stimulation channel to deliver neural stimulation pulses. The stimulation controller controls the delivery of the neural stimulation pulses using a plurality of stimulation parameters. The safety controller includes a safety-control event detection module and a safety response module. The safety-control event detection module detects a safety-control event and includes at least one of an energy detection module and a stimulation parameter detection module. The energy detection module detects a stimulation energy being the energy of one or more of the neural stimulation pulses delivered through the stimulation channel. The stimulation parameter detection module detects one or more parameter values each being a value of a parameter of the plurality of stimulation parameters. The safety response module adjusts the plurality of stimulation parameters in response to the detection of the safety-control event.

In one embodiment, a method for neural stimulation is provided. Neural stimulation pulses are delivered through at least one electrode. The delivery of the neural stimulation pulses is controlled using a plurality of stimulation parameters. A safety-control event is detected. The detection of the safety control events includes at least one of detection of a stimulation energy and detection of one or more parameter values. The stimulation energy is the energy of one or more neural stimulation pulses delivered through the electrode. The one or more parameter values are each a value of a parameter of the plurality of stimulation parameters. In response to the detection of the safety-control event, one or more parameters of the plurality of stimulation parameters are adjusted.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are not necessarily drawn to scale, like numerals describe similar components throughout the several views. The drawings illustrate generally, by way of example, various embodiments discussed in the present document.

DETAILED DESCRIPTION

Figure 1:
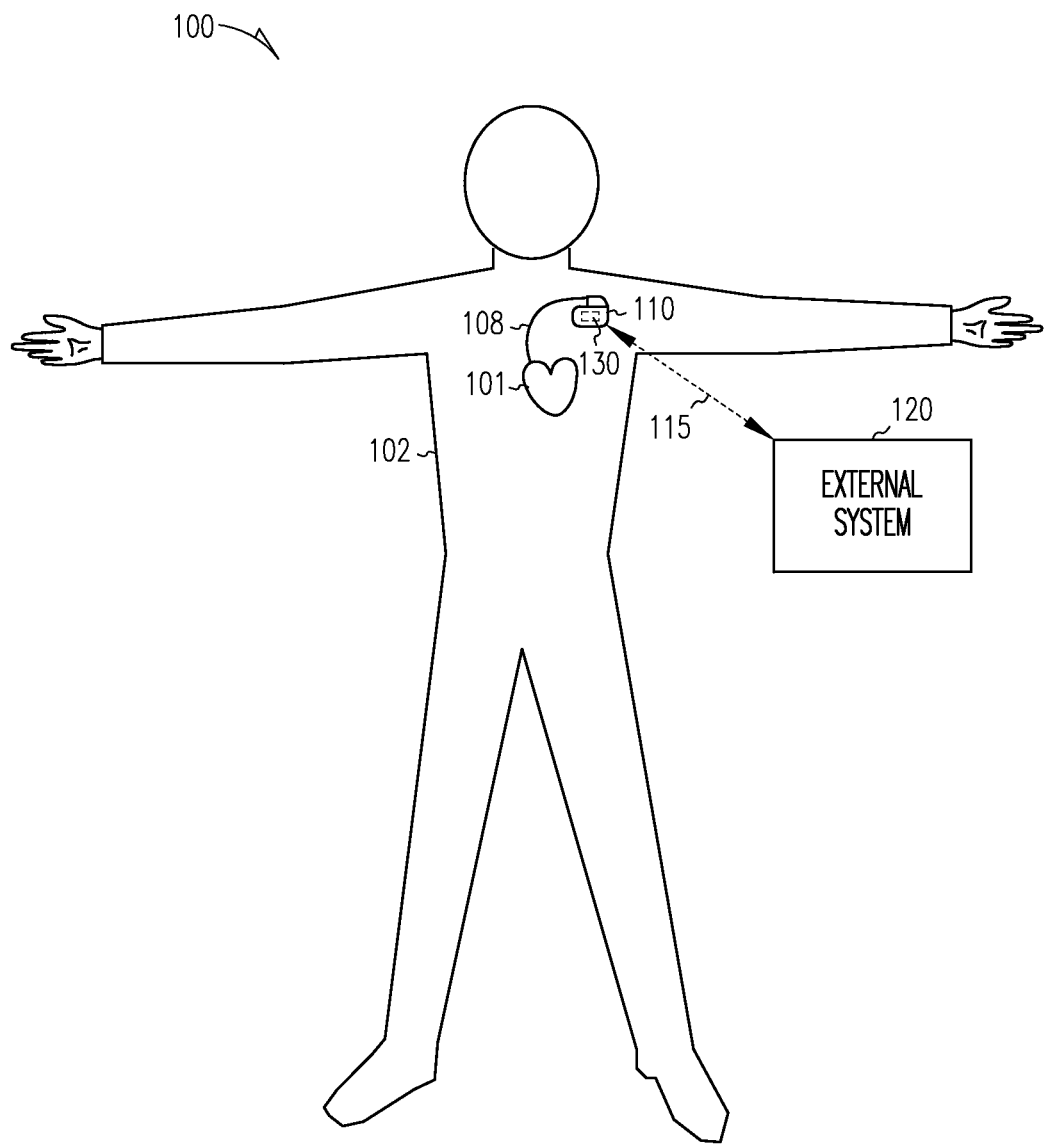
FIG. 1 is an illustration of an embodiment of a neural stimulation system and portions of an environment in which the neural stimulation system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a neural stimulation system for delivering neural stimulation pulses to one or more nerves to control physiological functions regulated by the one or more nerves. In various embodiments, the neural stimulation pulses are delivered to one or more nerves of the autonomic nervous system to control cardiac functions and hemodynamic performance. The potential benefits of delivering neural stimulation pulses to a patient with cardiac disorders are achieved or maximized when the therapy is adaptive to the patient's cardiac conditions and metabolic needs, both changing over time. A neural stimulation therapy optimized under certain circumstances may become potentially harmful when the circumstances change. For example, the intensity of a neural stimulation therapy may be adequate at one time but become excessive at another time, as the patient's cardiac conditions and therapeutic needs change. Excessive neural stimulation may injure the nerves being stimulated and/or cause unintended effects in the patient's cardiac, pulmonary, and other physiological conditions, including pain. In another example, a neural stimulation therapy adjusted to satisfy the instantaneous metabolic need for a heart failure patient to participate in an intense physical activity may result in further deterioration of myocardial tissue in that patient. According to the present subject matter, the neural stimulation system includes a safety control system to protect the patient from unintended delivery of the neural stimulation pulses and unintended effects associated with the delivery of the neural stimulation pulses. In one embodiment, the neural stimulation system monitors the energy delivered to each nerve or stimulation site to ensure that the total energy delivered over a certain period of time is within a safety limit. In another embodiment, the neural stimulation system monitors the actual stimulation parameters controlling the delivery of stimulation pulses to ensure that the parameters are within safety limits. In another embodiment, the neural stimulation system detects unintended effects that are possibly caused by the delivery of stimulation pulses and suspends or adjusts the delivery of stimulation pulses when one or more of the unintended effects are detected.

While neural stimulation of the autonomic nervous system for controlling cardiac functions and hemodynamic performance is specifically discussed in this document as a specific application, the present subject matter generally applies to electrical stimulation delivered to any one or more nerves for restoring and/or regulating physiological functions.

FIG. 1 is an illustration of an embodiment of a neural stimulation system 100 and portions of an environment in which system 100 is used. System 100 includes implantable medical device 110, a lead system 108, an external system 120, and a telemetry link 115.

As illustrated in FIG. 1, implantable medical device 110 is implanted in a body 102 of a patient to deliver neural stimulation pulses to the autonomic nervous system of the patient through lead system 108. Implantable medical device 110 includes a neural stimulation circuit 130. Neural stimulation circuit 130 delivers the neural stimulation pulses and includes a safety control system to prevent the patient from potential harmful effects associated with the delivery of the neural stimulation pulses. In various embodiments, as discussed in detail below, the safety control system detects safety-control events such as excessive or other inadequate deliveries of the neural stimulation pulses and/or unintended effects that develop in the patient with the delivery of the neural stimulation pulses. In response to a detection of such a safety-control event, the safety control system suspends or adjusts the delivery of the neural stimulation pulses. In various embodiments, implantable medical device 110 is also capable of sensing physiological signals and/or delivering therapies in addition to the neural stimulation. Examples of such additional therapies include cardiac pacing therapy, cardioversion/defibrillation therapy, cardiac resynchronization therapy (CRT), cardiac remodeling control therapy (RCT), drug therapy, cell therapy, and gene therapy. In various embodiments, implantable medical device 110 delivers the neural stimulation in coordination with one or more such additional therapies.

Lead system 108 provides electrical connections between implantable medical device 110 and one or more sympathetic and/or parasympathetic nerves that regulate the activities of a heart 101. In various embodiments, implantable medical device 110 provides neural stimulation to any one or more nerves through one or more implantable neural lead of lead system 108. Such implantable neural leads each include at least one electrode for sensing neural activities and/or delivering neural stimulation pulses. In various embodiments in addition to implantable neural leads, lead system 108 includes implantable cardiac leads allowing for the cardiac stimulation therapy such as cardiac pacing therapy, cardioversion/defibrillation therapy, CRT, and RCT and/or other implantable leads allowing for delivery of the drug therapy, cell therapy, and/or gene therapy.

External system 120 communicates with implantable medical device 110 via telemetry link 115. In one embodiment, external system 120 includes a programmer. In another embodiment, external system 120 is a patient management system including an external device communicating with implantable medical device 110 via telemetry link 115, a remote device in a relatively distant location, and a telecommunication network linking the external device and the remote device. The patient management system allows access to implantable medical device 110 from a remote location, for purposes such as monitoring patient status and adjusting therapies. Telemetry link 115 provides for data transmission from implantable medical device 110 to external system 120. This includes, for example, transmitting real-time physiological data acquired by implantable medical device 110, extracting physiological data acquired by and stored in implantable medical device 110, extracting patient history data such as occurrences of arrhythmias and therapy deliveries recorded in implantable medical device 110, and/or extracting data indicating an operational status of implantable medical device 110 (e.g., battery status and lead impedance). Telemetry link 115 also provides for data transmission from external system 120 to implantable medical device 110. This includes, for example, programming implantable medical device 110 to acquire physiological data, programming implantable medical device 110 to perform at least one self-diagnostic test (such as for a device operational status), and/or programming implantable medical device 110 to deliver one or more therapies and/or to adjust the delivery of one or more therapies.

Figure 2:
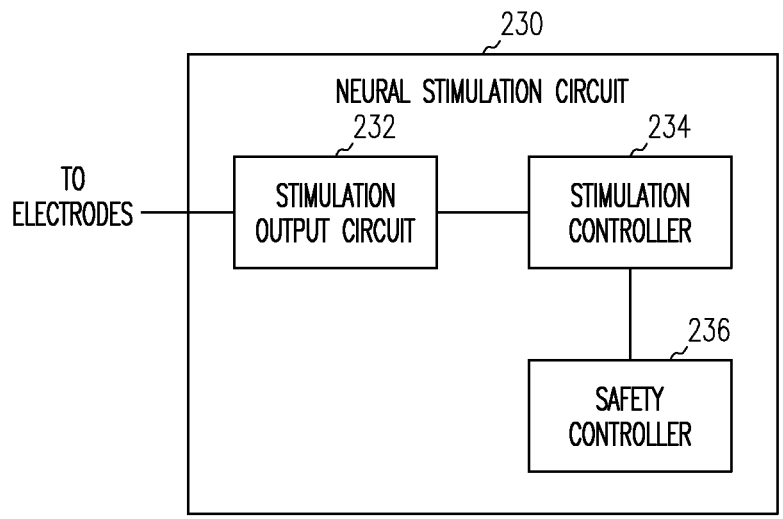
FIG. 2 is a block diagram illustrating an embodiment of a neural stimulation circuit of an implantable medical device.

FIG. 2 is a block diagram illustrating an embodiment of a neural stimulation circuit 230, which is a specific embodiment of neural stimulation circuit 130. Neural stimulation circuit 230 includes a stimulation output circuit 232, a stimulation controller 234, and a safety controller 236. Stimulation output circuit 232 includes one or more stimulation channels each to be connected to at least one electrode of lead system 108 for delivering neural stimulation pulses through that electrode. Stimulation controller 234 controls the delivery of the neural stimulation pulses by executing a neural stimulation algorithm using a plurality of stimulation parameters. Safety controller 236 detects safety-control events and adjusts one or more stimulation parameters of the plurality of stimulation parameters in response to the detection of each safety-control event.

The stimulation parameters control the intensity and the timing of delivery of the neural stimulation pulses. In one embodiment, the stimulation parameters include pulse amplitude, pulse width, and stimulation frequency. The pulse amplitude is the amplitude of a neural stimulation pulse. The pulse width is the width of a neural stimulation pulse. The stimulation frequency is the frequency at which the neural stimulation pulses are delivered. Alternatively, the parameter controlling the stimulation frequency is given as stimulation interval (or inter-pulse interval), which is the time interval between two successively delivered stimulation pulses. In one embodiment, the neural stimulation is delivered as bursts of the neural stimulation pulses. The stimulation parameters further include burst duration, burst interval, and/or stimulation duty cycle. The burst duration is a time interval during which a burst of the neural stimulation pulses is delivered. The burst interval is the time interval between the beginnings of two successively delivered bursts of the neural stimulation pulses. Alternatively, the parameter controlling burst interval is the burst frequency, which is the frequency at which the delivery of a burst of the neural stimulation pulses is initiated. In a specific embodiment, the delivery of the bursts of the neural stimulation pulses is synchronized to cardiac cycles, and the burst interval dynamically changes as a function of the heart rate or cardiac cycle length. The stimulation duty cycle is the ratio of the burst duration to the burst interval. The stimulation parameters are further discussed in detail below with reference to FIG. 14.

Figure 3:
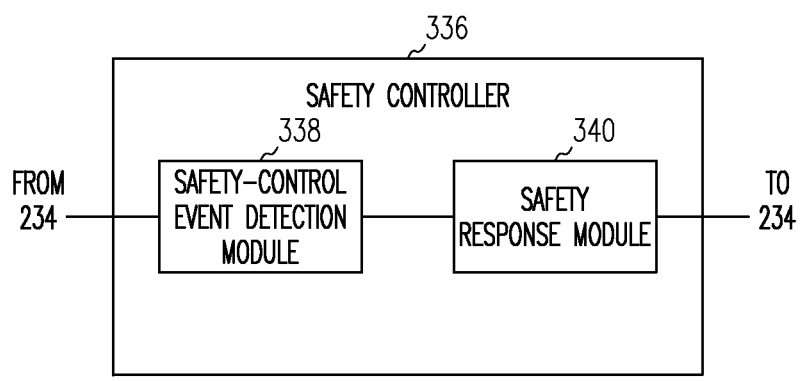
FIG. 3 is a block diagram illustrating an embodiment of a safety controller of the neural stimulation circuit.

FIG. 3 is a block diagram illustrating an embodiment of a safety controller 336, which is a specific embodiment of safety controller 236. Safety controller 336 includes a safety-control event detection module 338 and a safety response module 340. Safety-control event detection module 338 detects safety-control events. Such safety-control events are associated with values of the stimulation parameters. The detection of such a safety-control event indicates that the magnitude of the neural stimulation has reached a degree considered as excessive or that at least one unintended effect has developed during the neural stimulation. Safety response module 340 adjusts the one or more stimulation parameters in response to the detection of the safety-control event. The one or more stimulation parameters are adjusted to stop or suspend the neural stimulation or to reduce the intensity of the neural stimulation. In one embodiment, safety-control event detection module 338 and safety response module 340 are implemented as a runaway protection circuit. When the magnitude of the neural stimulation becomes excessive, the runaway protection circuit cuts off the delivery of the neural stimulation. In a specific embodiment, the runaway protection circuit includes one or more of a stimulation amplitude limiter and a stimulation frequency limiter. The stimulation amplitude limiter cuts off the amplitude of neural stimulation pulses at a predetermined threshold amplitude whenever the amplitude exceeds that threshold amplitude. The stimulation frequency limiter cuts off the frequency at which the neural stimulation pulses are delivered at a predetermined threshold frequency whenever the frequency exceeds that threshold frequency.

Figure 4:
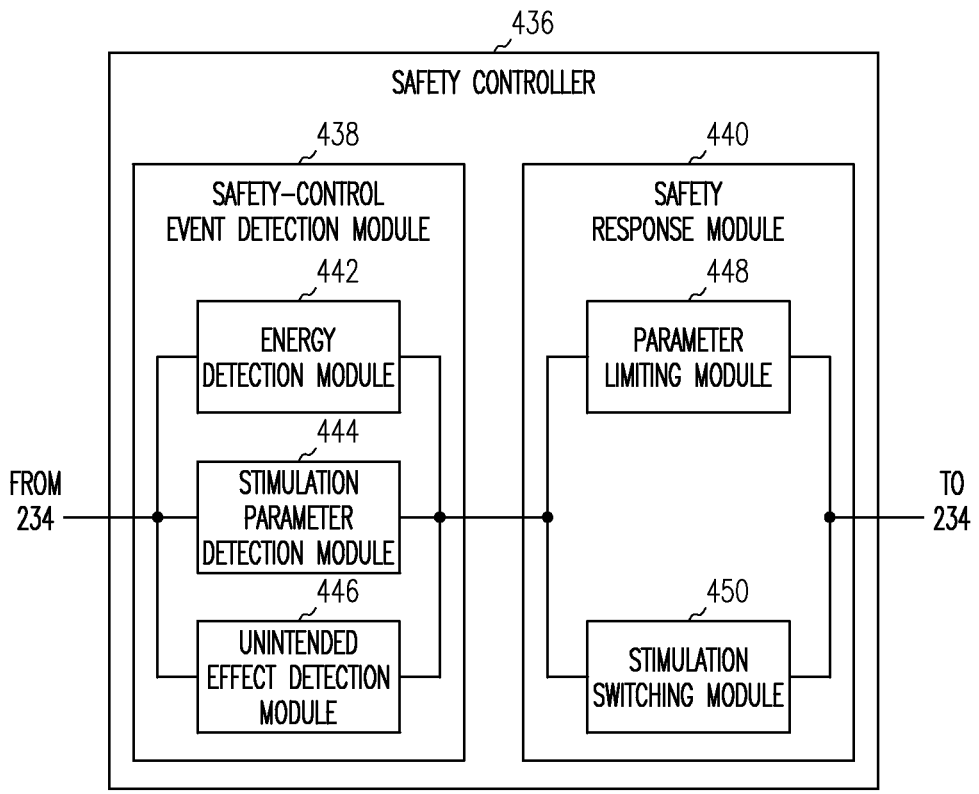
FIG. 4 is a block diagram illustrating a specific embodiment of the safety controller.

FIG. 4 is a block diagram illustrating a safety controller 436, which is a specific embodiment of safety controller 336. Safety controller 436 includes a safety-control event detection module 438 and a safety response module 440.

Safety-control event detection module 438 is a specific embodiment of safety-control event detection module 338. In one embodiment, as illustrated in FIG. 4, safety-control event detection module 438 includes an energy detection module 442, a stimulation parameter detection module 444, and an unintended effect detection module 446. In various other embodiments, safety-control event detection module 438 includes any one, or a combination of any two, of energy detection module 442, stimulation parameter detecting module 444, and unintended effect detection module 446. In a specific embodiment, safety-control event detection module 438 includes energy detection module 442. In another specific embodiment, safety-control event detection module 438 includes stimulation parameter detecting module 444. In another specific embodiment, safety-control event detection module 438 includes unintended effect detection module 446. In another specific embodiment, safety-control event detection module 438 includes energy detection module 442 and stimulation parameter detecting module 444. In another specific embodiment, safety-control event detection module 438 includes energy detection module 442 and unintended effect detection module 446. In another specific embodiment, safety-control event detection module 438 includes stimulation parameter detecting module 444 and unintended effect detection module 446.

Energy detection module 442 detects a stimulation energy being an energy carried in one or more neural stimulation pulses. Safety-control event detection module 438 indicates a detection of the safety-control event when the stimulation energy exceeds a predetermined threshold energy. In one embodiment, energy detection module 442 detects a stimulation energy being the energy of each of the neural stimulation pulses. Safety-control event detection module 438 indicates a detection of the safety-control event when the energy of any individual stimulation pulse exceeds a predetermined threshold energy. In another embodiment, energy detection module 442 detects a stimulation energy being the total energy of the neural stimulation pulses delivered through a stimulation channel of stimulation output circuit 232 over a predetermined period of time. Safety-control event detection module 438 indicates a detection of the safety-control event when the total energy delivered over the predetermined period of time exceeds a predetermined threshold energy. This prevents excessive delivery of energy due to excessive stimulation amplitude and/or frequency.

Stimulation parameter detection module 444 detects values of one or more stimulation parameters of the plurality of stimulation parameters controlling the delivery of the neural stimulation pulses. The values of the one or more stimulation parameters to be detected include abnormal values that become effective because of various system defects or accidents. One example is a "runaway stimulation" during which the delivery of the neural stimulation pulses is no longer in accordance with a predetermined stimulation algorithm that is being executed by stimulation controller 234. Safety-control event detection module 438 indicates a detection of the safety-control event when at least the value of one stimulation parameter exceeds a threshold value of that stimulation parameter. In one embodiment, the threshold value is predetermined and stored. In another embodiment, safety-control event detection module 438 includes a threshold adjustment module that dynamically adjusts the threshold value based on at least the value of another stimulation parameter. In another embodiment, safety-control event detection module 438 includes a look-up table relating the threshold value to at least the value of another stimulation parameter. In a specific embodiment, safety-control event detection module 438 indicates the detection of the safety-control event when a combination of at least the value of a first stimulation parameter and the value of a second stimulation parameter exceed a combination of a threshold value of the first stimulation parameter and a threshold value of the second stimulation parameter. The look-up table contains a plurality of combinations of the threshold value of the first stimulation parameter and the threshold value of the second stimulation parameter.

Unintended effect detection module 446 detects unintended effects associated with the delivery of the neural stimulation pulses. An unintended effect includes a side effect considered intolerable, unacceptable, and/or potentially injurious to the patient. Safety-control event detection module 438 indicates a detection of the safety-control event when one of the unintended effects is detected. In one embodiment, unintended effect detection module 446 includes a physiological parameter detection module that detects a physiological parameter indicative of whether an unintended effect is present. The physiological parameter detection module senses the value of the physiological parameter, compare the sensed value to a normal value range including one or more threshold values, and indicate a detection of the unintended effect when the sensed value falls out of the normal value range. Examples of such a physiological parameters include heart rate, blood pressure, stroke volume, thoracic impedance, acceleration, acoustic parameter indicative coughing, and parameter related to an electromyogram. For example, an abnormally low heart rate is an unintended effect indicative a need to suspend or reduce the intensity of stimulation to the parasympathetic nervous system. The stroke volume and thoracic impedance are used to monitor respiratory rate, volume, and pattern, which may be affected by the neural stimulation. The acceleration and acoustic parameters indicate coughing, which may be resulted from the neural stimulation. The parameter related to the electromyogram, such as the amplitude of the electromyogram, indicates whether the neural stimulation unintentionally activates certain muscle fibers or muscle groups. In one embodiment, unintended effect detection module 446 senses a signal indicative of the unintended effect and detects the unintended effect from that signal. For example, unintended effect detection module 446 senses a cardiac signal such as an electrogram, measures a heart rate from the electrogram, and detects the unintended effect when the heart rate drops below a predetermined minimum heart rate. In another embodiment, unintended effect detection module receives a signal indicative of the detection of the unintended effect. In a specific embodiment, the signal is produced by another component of system 100 that is external to safety controller 436. For example, system 100 may include a pacemaker that detects abnormally low heart rates and communicates to unintended effect detection module 446 when an abnormally low heart rate is detected. In another embodiment, the signal is received by external system 120, which transmits the received signal to unintended effect detection module 446. For example, a patient feels the occurrence of an unintended effect (such as pain) and enters a patient command using a patient input device of external system 120. External system 120 then communicates the patient command to unintended effect detection module 446. In one embodiment, unintended effect detection module 446 includes an unintended cardiac event detector to detect an unintended cardiac event, such as bradycardia, asystole, hypotension, atrial tachyarrhythmias including atrial flutter and atrial fibrillation, and ventricular tachyarrhythmias including ventricular tachycardia and ventricular fibrillation. In one embodiment, unintended effect detection module 446 includes an unintended pulmonary event detector to detect an unintended pulmonary event, such as dyspnea, coughing, apnea, and hypopnea. In various embodiments, unintended effect detection module 446 detects one or more of unintended effects associated with electrical stimulation of autonomic nervous system, including, but not limited to, cardiac arrhythmias, asystole, hypotension, infection, nerve paralysis, hypesthesia, facial paresis, vocal cord paralysis, facial paralysis, diaphragm paralysis, recurrent laryngeal nerve injury, urinary retention, low-grade fever, voice alteration, substantial increase in coughing, pharyngitis, paresthesia, dyspnea, apnea, hypopnea, dyspepsia, nausea, laryngismus, and pain. Some of these unintended effects, such as infection, low-grade fever, and pain, are practically difficult to detect within an implantable device but are suitable for external detection or diagnosis by an external device, the patient, or a physician or other caregiver. Thus, in various embodiments, unintended effect detection module 446 detects such unintended effects by receiving signals or commands from the external device, the patient, and/or the physician or other caregiver through external system 120.

Safety response module 440 is a specific embodiment of safety response module 340. In response to the detection of the safety-control event by safety-control event detection module 438, safety response module 440 adjusts one or more stimulation parameters controlling the delivery of the neural stimulation pulses. In one embodiment, as illustrated in FIG. 4, safety response module 440 includes a parameter limiting module 448 and a stimulation switching module 450. In various other embodiments, safety response module 440 includes any one of parameter limiting module 448 and stimulation switching module 450. In a specific embodiment, safety response module 440 includes parameter limiting module 448. In another specific embodiment, safety response module 440 includes stimulation switching module 450.

Parameter limiting module 448 sets a value of a stimulation parameter to a threshold value of that parameter when the value of the stimulation parameter exceeds the threshold value. The threshold value is provided as described above with respect to stimulation parameter detection module 444.

In one embodiment, parameter limiting module 448 is an intensity reduction module that adjusts one or more stimulation parameters to reduce the intensity of the neural stimulation while the safety-control event is being detected. The intensity reduction module reduces the intensity of the neural stimulation by, for example, reducing the value of one or more of pulse amplitude, pulse width, stimulation frequency, burst duration, and stimulation duty cycle.

Stimulation switching module 450 acts as an on/off switch that stops and starts the delivery of the neural stimulation pulses. In one embodiment, stimulation switching module 450 adjusts one or more stimulation parameters to suspend the delivery of the neural stimulation pulses while the safety-control event is being detected.

Figure 5:
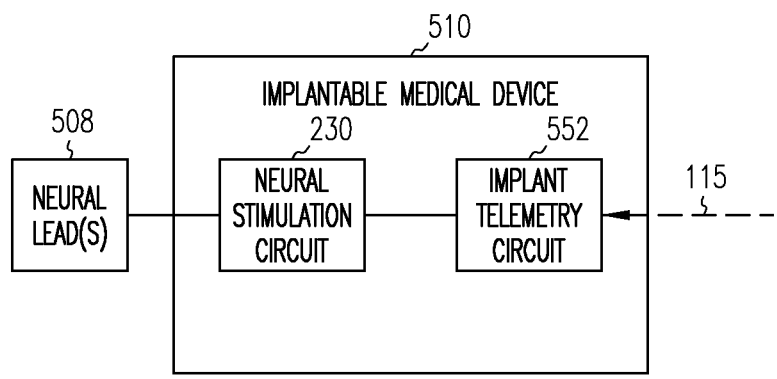
FIG. 5 is a block diagram illustrating an embodiment of an implantable medical device including the neural stimulation circuit.

FIG. 5 is a block diagram illustrating an embodiment of an implantable medical device 510, which is a specific embodiment of implantable medical device 110. Implantable medical device 510 includes neural stimulation circuit 230 and implant telemetry circuit 552. One or more neural leads 508 of lead system 108 provide for one or more electrical connections between neural stimulation circuit 230 and body 102 through which the neural stimulation pulses are delivered. Implant telemetry circuit 552 allows implantable medical device 510 to communicate with external system 120 through telemetry link 115.

Neural lead(s) 508 allow sensing of neural activities from, and/or delivery of neural stimulation pulse to, one or more nerves of the autonomic nervous system including the sympathetic and parasympathetic nerves. Examples of neural lead(s) 508 include, but are not limited to, an expandable stimulation lead having an electrode for placement in a pulmonary artery in a proximity of a high concentration of baroreceptors, a transvascular lead having an electrode for placement proximal to a cardiac fat pad, an epicardial lead having an electrode for placement in a cardiac fat pad, a lead having a cuff electrode for placement around an aortic, carotid, or vagus nerve, an intravascularly fed lead having an electrode for placement proximal to the aortic, carotid, or vagus nerve for transvascularly delivering the neural stimulation pulses that nerve, and a lead having an electrode for placement in a spinal cord.

Figure 6:
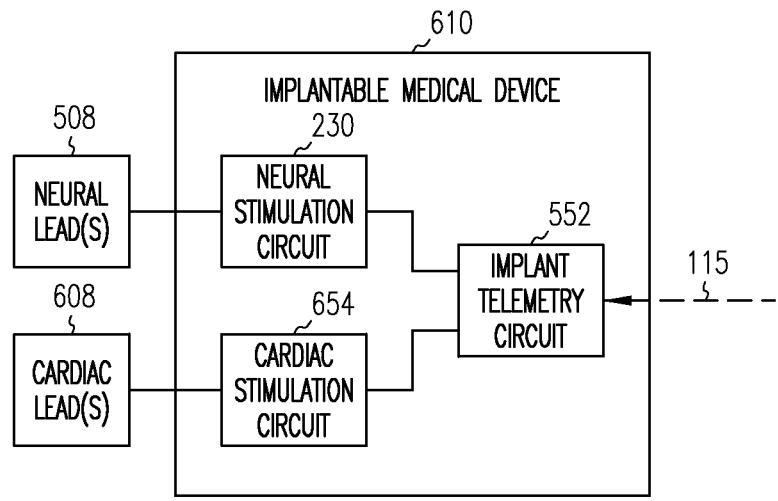
FIG. 6 is a block diagram illustrating an embodiment of an implantable medical device including the neural stimulation circuit and a cardiac stimulation circuit.

FIG. 6 is a block diagram illustrating an embodiment of an implantable medical device 610, which is another specific embodiment of implantable medical device 110. Implantable medical device 610 is an integrated cardiac and neural stimulation device and includes neural stimulation circuit 230, a cardiac stimulation circuit 654, and implant telemetry circuit 552.

Cardiac stimulation circuit 654 delivers cardiac stimulation pulses to heart 101 through one or more cardiac leads 608 of lead system 108. Examples of the cardiac stimulation circuit 654 include a pacing circuit, a cardioversion/defibrillation circuit, a CRT circuit, and an RCT circuit. Cardiac stimulation circuit 654 also provides for sensing of one or more cardiac signals including electrograms. In one embodiment, cardiac stimulation circuit 654 provides the one or more signals indicative the unintended effects associated with the neural stimulation delivered by neural stimulation circuit 230. Cardiac lead(s) 608 include one or more implantable cardiac stimulation leads each including at least one endocardial or epicardial electrode configured for sensing cardiac activities from, and/or delivering cardiac stimulation pulses to, heart 101. In one embodiment, neural lead(s) 508 and cardiac lead(s) 608 include one or more integrated neural and cardiac leads. Such an integrated neural and cardiac lead includes electrodes for sensing neural activities, sensing cardiac activities, delivering neural stimulation pulses, and delivering cardiac stimulation pulses.

In various embodiments, implantable medical device 510 or 610 further includes one or more of a drug delivery device, a biological therapy device, and any other device. In various embodiments, functions of such devices and/or cardiac stimulation circuit 654 supplement the functions of neural stimulation circuit 230.

Figure 7:
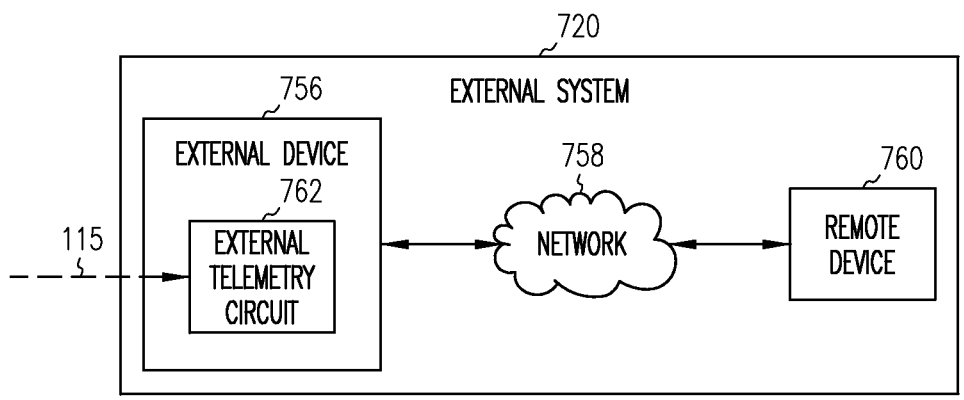
FIG. 7 is a block diagram illustrating an embodiment of the external system.

FIG. 7 is a block diagram illustrating an embodiment of an external system 720, which is a specific embodiment of external system 120. As illustrated in FIG. 7, external system 720 is a patient management system including an external device 756, a telecommunication network 758, and a remote device 760. External device 756 is placed within the vicinity of implantable medical device 110 and includes external telemetry circuit 762 to communicate with implantable medical device 110 via telemetry link 115. Remote device 760 is in a remote location and communicates with external device 756 through network 758, thus allowing a physician or other caregiver to monitor and treat a patient from a distant location and/or allowing access to various treatment resources from the remote location.

In one embodiment, external system 720 includes an input device to receive the signal indicative of the detection of an unintended effect associated with neural stimulation, as discussed above with reference to FIG. 4. The input device allows a physician or other caregiver or the patient to stop the neural stimulation or reduce the intensity of the neural stimulation when an unintended effect is diagnosed, observed, or felt. In one embodiment, external device 756 includes the input device. In another embodiment, remote device 760 includes the input device in remote device. In another embodiment, external device 756 and remote device 760 each include such an input device to receive the signal indicative of the detection of the unintended effect.

According to the present subject matter, neural stimulation pulses are delivered to the sympathetic nervous system and the parasympathetic nervous system through one or more neural leads. In various embodiments, neural signals are sensed from the sympathetic nervous system and the parasympathetic nervous system through the one or more neural leads. Examples of sites to which the neural stimulation pulses are delivered and from which neural signals are sensed include a site in a pulmonary artery in a proximity of a high concentration of baroreceptors, a cardiac fat pad, an aortic nerve, a carotid nerve, a vagus nerve, a vascular site proximal to the aortic, carotid, or vagus nerve, and sites in the spinal cord on or near the sympathetic ganglia, or nerves to or from the sympathetic ganglia. Electrodes of the one or more neural leads are placed in one or more such sites for neural sensing and stimulation.

A brief discussion of the physiology related to baroreceptors and chemoreceptors is provided below. This brief discussion introduces the autonomic nervous system, baroreflex, and chemoreceptors to provide an understanding of placement of the electrodes (also referred to as neural traffic sensors) of the neural leads.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 8B:
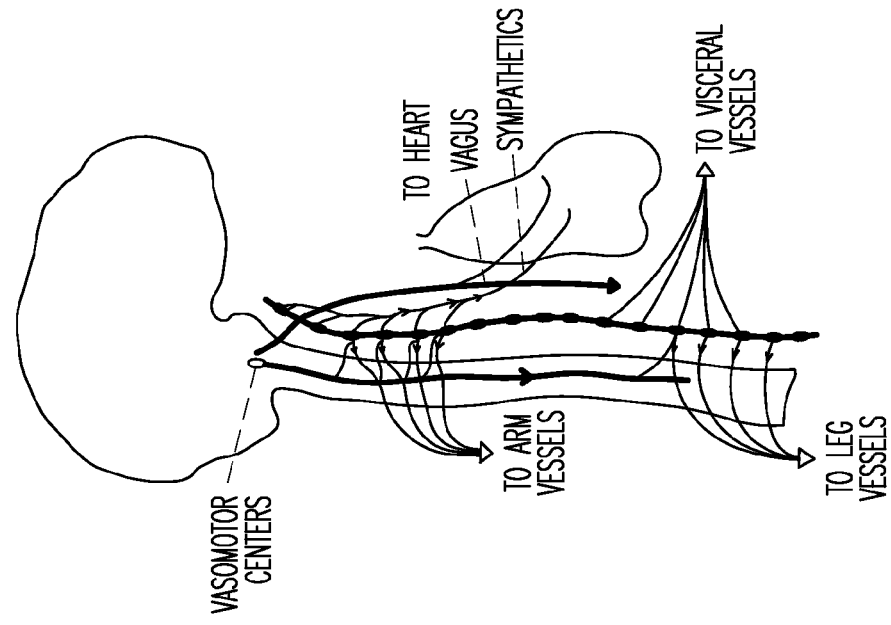
FIGS. 8A and 8B are illustrations of neural mechanisms for peripheral vascular control.
Figure 8A:
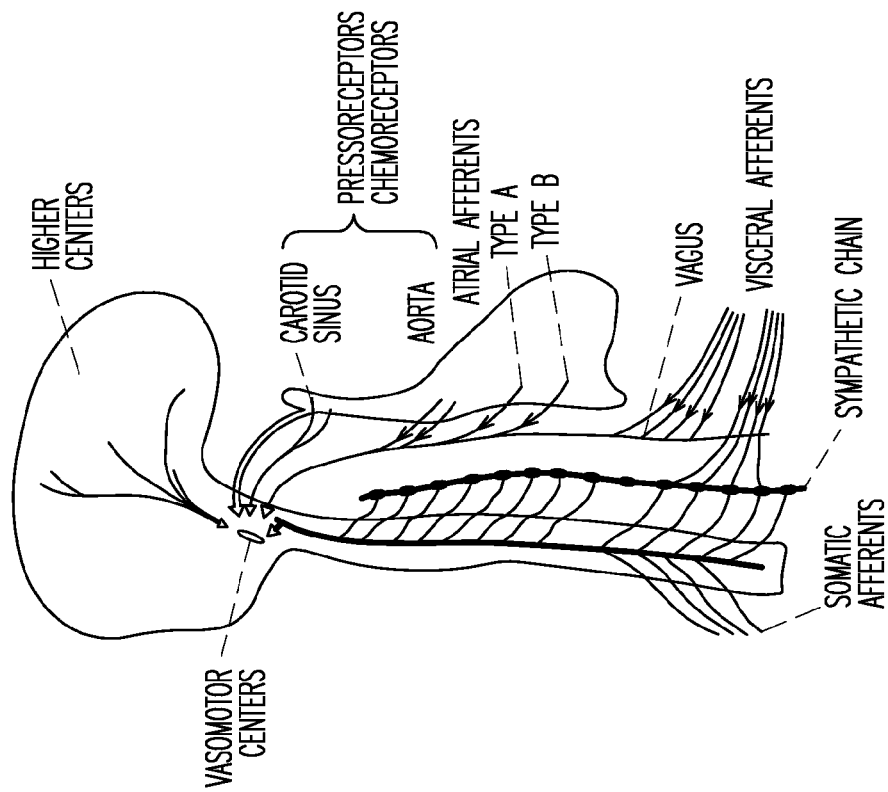

In various embodiments, neural stimulation is applied to affect the heart rate, blood pressure, vasodilation, and vasoconstriction. The heart rate and contractile strength is increased when excitatory stimulation is applied to the sympathetic nervous system and when inhibitory stimulation is applied the parasympathetic nervous system, and is decreased when inhibitory stimulation is applied the sympathetic nervous system or when excitatory stimulation is applied the sympathetic nervous system. In various embodiments, nerve traffic is also sensed to provide a surrogate parameter for another physiological parameter, such as heart rate, blood pressure and the like. FIGS. 8A and 8B illustrate neural mechanisms for peripheral vascular control. FIG. 8A generally illustrates afferent nerves to vasomotor centers. An afferent nerve conveys impulses toward a nerve center. A vasomotor center relates to nerves that dilate and constrict blood vessels to control the size of the blood vessels. FIG. 8B generally illustrates efferent nerves from vasomotor centers. An efferent nerve conveys impulses away from a nerve center.

Stimulation of the sympathetic and parasympathetic nervous systems is known to have effects other than heart rate, contractile strength, and blood pressure. For example, excitatory stimulation of the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Excitatory stimulation of the parasympathetic nervous system and/or inhibitory stimulation of the sympathetic nervous system constrict the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems. Additionally, sensing of nerve traffic for use as a surrogate parameter of a physiological parameter can depend on a number of physiological parameters. Various embodiments of the present subject matter perturb the physiological system with precisely located neural stimulation, and monitor the nerve traffic response to the stimulation.

A pressoreceptive region or field is capable of sensing changes in pressure, such as changes in blood pressure. Pressoreceptor regions are referred to herein as baroreceptors, which generally include any sensors of pressure changes. For example, baroreceptors include afferent nerves and further include sensory nerve endings that provide baroreceptor fields that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, which excites the parasympathetic nervous system causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. Centrally mediated reflex pathways modulate cardiac rate, contractility and excitability. Baroreceptors and chemoreceptors in the heart, great vessels, and lungs, transmit neural signals reflective of cardiac activity through vagal and afferent fibers to the central nervous system. Thus, physiological parameters, such as systemic arterial pressure, can be determined based on nerve traffic. Such pressure information, for example, provides useful feedback information to guide therapy such as neural therapy or cardiac stimulation therapy such as CRT.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Afferent nerves can also be electrically stimulated to induce a baroreflex, which inhibits the sympathetic nerve activity and stimulates parasympathetic nerve activity. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptors are naturally stimulated by internal pressure and the stretching of vessel wall (e.g. arterial wall).

Some aspects of the present subject matter locally sense specific nerve endings in vessel walls rather than or in addition to afferent and/or efferent nerve trunks. For example, some embodiments sense baroreceptor sites or fields in the pulmonary artery. Some embodiments of the present subject matter involve sensing baroreceptor sites or nerve endings in the aorta, the chambers of the heart, some embodiments of the present subject matter involve sensing efferent pathways such as the fat pads of the heart, and some embodiments of the present subject matter involve stimulating an afferent nerve trunk, such as the vagus, carotid and aortic nerves. Various embodiments involve combinations of sensing nerve ending, sensing efferent nerve pathways and sensing afferent nerve pathways. Some embodiments sense nerve trunks using a cuff electrode, and some embodiments sense nerve trunks using an intravascular lead positioned in a blood vessel proximate to the nerve. Examples of afferent nerve trunks include the vagus, aortic and carotid nerves. Examples of efferent nerve trunks include the cardiac branches off the vagus nerve. Stimulation of efferent nerves such as these cardiac branches or the nerves in cardiac fat pads conveys nervous impulses to an effector, and thus do not use the baroreflex negative feedback of the central nervous system, which responds to nerve activity on afferent nerves with nerve activity on efferent nerves. Some embodiments sense neural traffic at any of the above-identified neural stimulation sites.

Figure 9B:
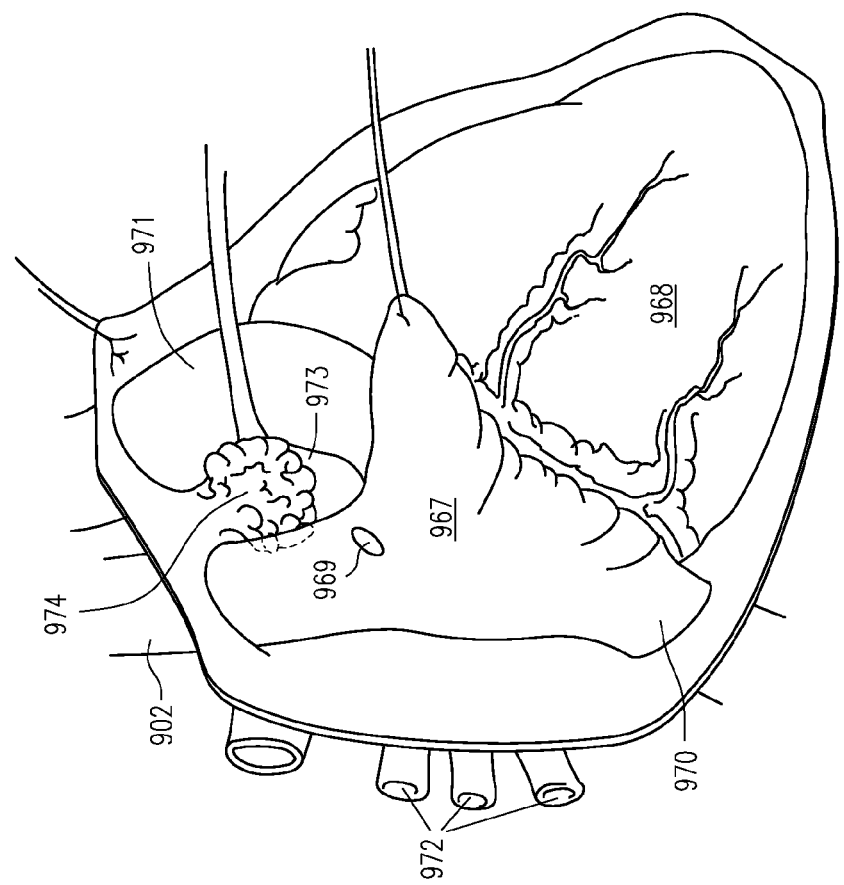
FIGS. 9A-C are illustrations of a heart.
Figure 9A:
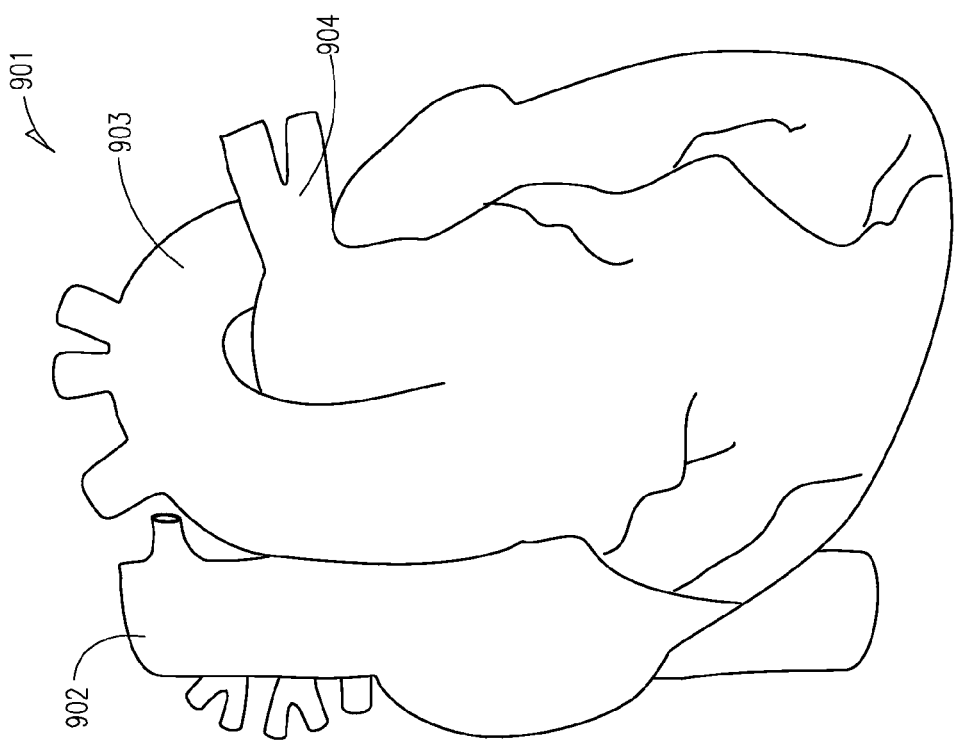
Figure 9C:
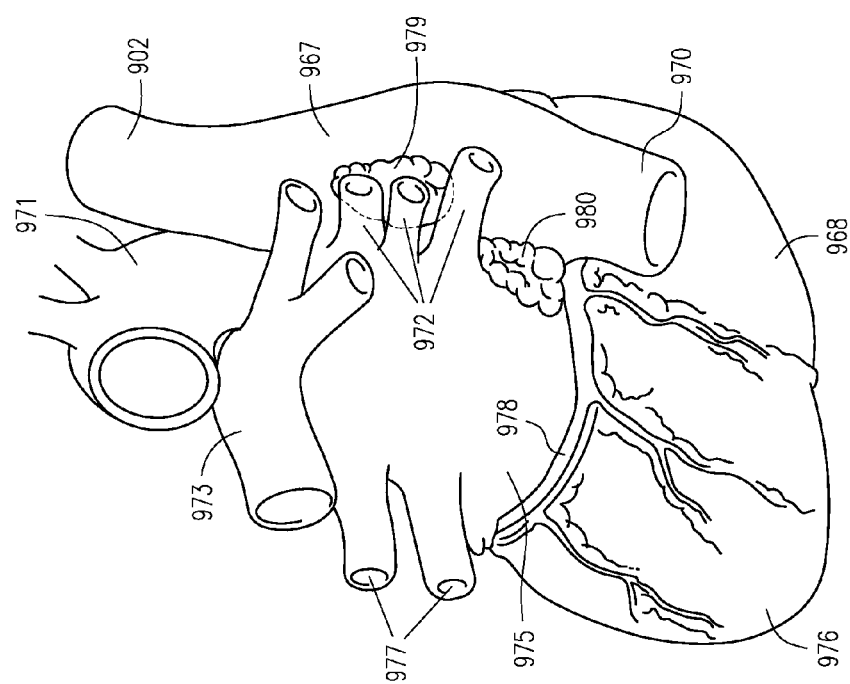

FIGS. 9A-9C illustrate a heart. As illustrated in FIG. 9A, the heart 901 includes a superior vena cava 902, an aortic arch 903, and a pulmonary artery 904. As is discussed in more detail below, pulmonary artery 904 includes baroreceptors. A lead is capable of being intravascularly inserted through a peripheral vein and through the tricuspid valve into the right ventricle of the heart (not expressly shown in the figure) similar to a cardiac pacing lead, and continue from the right ventricle through the pulmonary valve into the pulmonary artery. A portion of the pulmonary artery and aorta are proximate to each other. Various embodiments sense neural activity by the baroreceptor in the aorta using a lead intravascularly positioned in the pulmonary artery. Some embodiments also stimulate baroreceptors in the aorta. Aspects of the present subject matter provide a relatively noninvasive surgical technique to implant a neural traffic sensor, with or without a baroreceptor stimulator, intravascularly into the pulmonary artery.

FIGS. 9B-9C illustrate the right side and left side of the heart, respectively, and further illustrate cardiac fat pads. FIG. 9B illustrates the right atrium 967, right ventricle 968, sinoatrial node 969, superior vena cava 902, inferior vena cava 970, aorta 971, right pulmonary veins 972, and right pulmonary artery 973. FIG. 9B also illustrates a cardiac fat pad 974 between superior vena cava 902 and aorta 971. Autonomic ganglia in cardiac fat pad 974 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the right pulmonary artery or superior vena cava, for example. FIG. 9C illustrates the left atrium 975, left ventricle 976, right atrium 967, right ventricle 968, superior vena cava 902, inferior vena cava 970, aorta 971, right pulmonary veins 972, left pulmonary vein 977, right pulmonary artery 973, and coronary sinus 978. FIG. 9C also illustrates a cardiac fat pad 979 located proximate to the right cardiac veins and a cardiac fat pad 980 located proximate to inferior vena cava 970 and left atrium 975. Autonomic ganglia in cardiac fat pad 979 are stimulated and/or nerve traffic is sensed in some embodiments using an electrode screwed or otherwise inserted into cardiac fat pad 979, and are stimulated and/or nerve traffic is sensed in some embodiments using an intravenously-fed lead proximately positioned to the fat pad in a vessel such as right pulmonary artery 973 or right pulmonary vein 972, for example. Autonomic ganglia in cardiac fat pad 980 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as inferior vena cava 970 or coronary sinus 978 or a lead in left atrium 975, for example.

Figure 10:
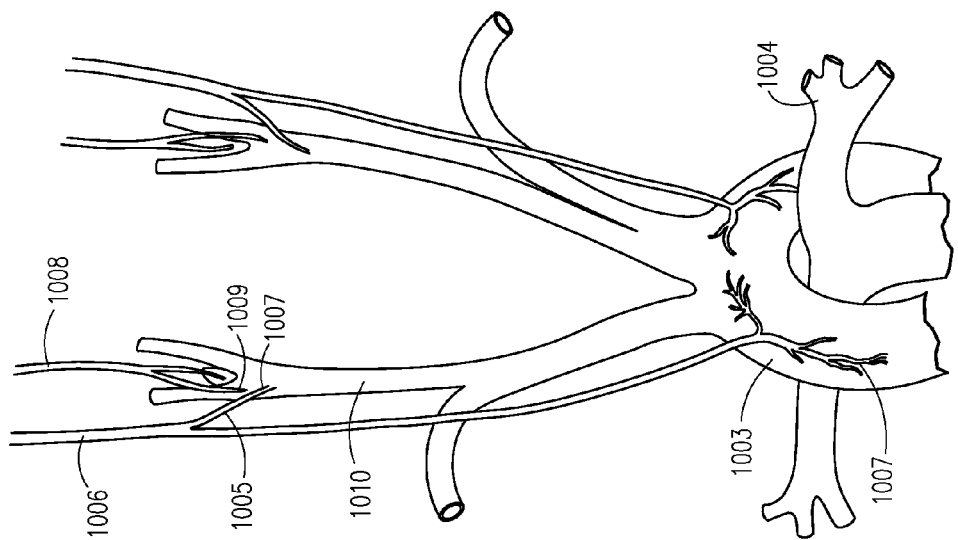
FIG. 10 is an illustration of baroreceptors and afferent nerves in the area of the carotid sinuses and aortic arch.

FIG. 10 illustrates baroreceptors in the area of the carotid sinus 1005, aortic arch 1003 and pulmonary artery 1004. The aortic arch 1003 and pulmonary artery 1004 were previously illustrated with respect to the heart in FIG. 9A. As illustrated in FIG. 10, the vagus nerve 1006 extends and provides sensory nerve endings 1007 that function as baroreceptors in the aortic arch 1003, in carotid sinus 1005 and in the common carotid artery 1010. The glossopharyngeal nerve 1008 provides nerve endings 1009 that function as baroreceptors in carotid sinus 1005. These nerve endings 1007 and 1009, for example, are sensitive to stretching of the wall resulting from increased pressure from within. Activation of these nerve endings reduces pressure. Although not illustrated in the figures, the fat pads and the atrial and ventricular chambers of the heart also include baroreceptors. Cuffs have been placed around afferent nerve trunks, such as the vagal nerve, leading from baroreceptors to vasomotor centers to stimulate the baroreflex. In various embodiments, afferent nerve trunks are stimulated, and/or nerve traffic from the afferent nerve trunks are sensed, using a cuff or intravascularly-fed lead positioned in a blood vessel proximate to the afferent nerves.

Figure 11:
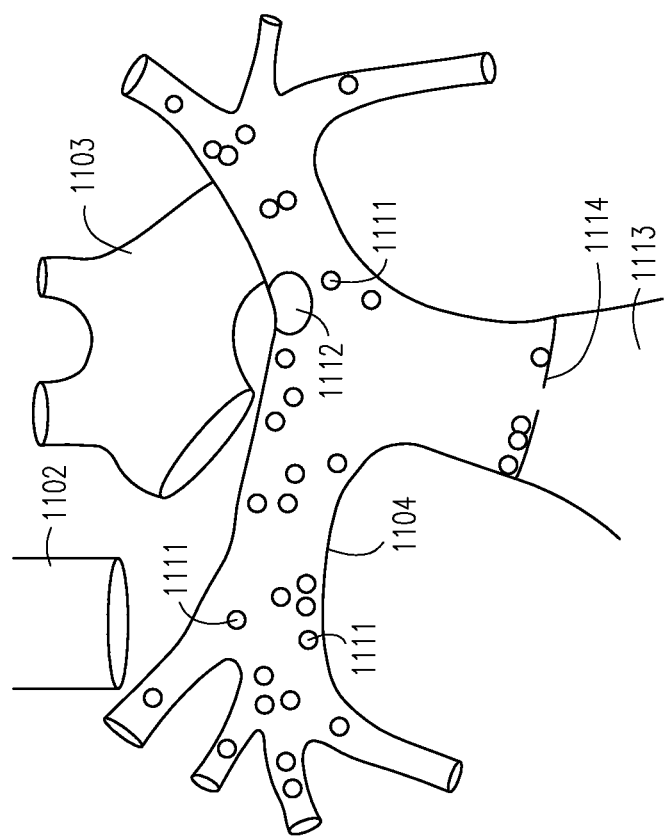
FIG. 11 is an illustration of baroreceptors in and around the pulmonary artery.

FIG. 11 illustrates baroreceptors in and around a pulmonary artery 1104. The superior vena cava 1102 and the aortic arch 1103 are also illustrated. As illustrated, pulmonary artery 1104 includes a number of baroreceptors 1111, as generally indicated by the dark area. Furthermore, a cluster of closely spaced baroreceptors is situated near the attachment of the ligamentum arteriosum 1112. FIG. 11 also illustrates the right ventricle 1113 of the heart, and the pulmonary valve 1114 separating right ventricle 1113 from pulmonary artery 1104. According to various embodiments of the present subject matter, a lead is inserted through a peripheral vein and threaded through the tricuspid valve into the right ventricle, and from right ventricle 1113 through pulmonary valve 1114 and into pulmonary artery 1104 to stimulate baroreceptors and/or sense nerve traffic from the baroreceptors in and/or around the pulmonary artery. In various embodiments, for example, the lead is positioned to stimulate the cluster of baroreceptors and/or sense nerve traffic near ligamentum arteriosum 1112.

Figure 12:
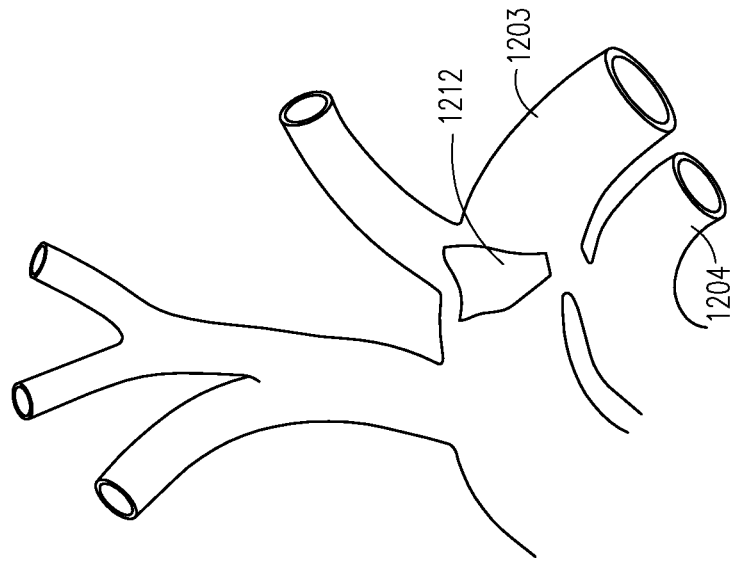
FIG. 12 is an illustration of baroreceptor fields in the aortic arch, the ligamentum arteriosum and the trunk of the pulmonary artery.

FIG. 12 illustrates baroreceptor fields 1212 in the aortic arch 1203, near the ligamentum arteriosum and the trunk of the pulmonary artery 1204. Some embodiments position the lead in the pulmonary artery to stimulate baroreceptor sites and/or sense nerve traffic in the aorta and/or cardiac fat pads, such as are illustrated in FIGS. 9B and 9C.

Various embodiments of the present subject matter sense nerve traffic corresponding to chemoreceptors. The carotid and aortic bodies provide a concentration of cardiovascular chemoreceptors. The carotid body lies deep to the bifurcation of the common carotid artery or somewhat between the two branches. The carotid body is a small, flattened, oval structure, 2 to 5 mm in diameter, with a characteristic structure composed of epithelioid cells, which are in close relation to capillary sinusoids, and an abundance of nerve fibers. Surrounding the carotid body is a delicate fibrous capsule. It is part of the visceral afferent system of the body, containing chemoreceptor endings that respond to low levels of oxygen in the blood or high levels of carbon dioxide and lowered pH of the blood. It is supplied by nerve fibers from both the glossopharyngeal and vagus nerves.

The aortic bodies (glomera aortica) are chemoreceptors similar to the carotid bodies. Afferent fibers from the aortic bodies run in the right vagus and have cell bodies in the inferior ganglion. The supracardial bodies (aortic paraganglia) are also chemoreceptors with their afferent fibers in the left vagus and cell bodies in the inferior ganglion.

In various embodiments of the present subject matter, neural signals are sensed, and neural therapies are delivered, by an implantable system including an implantable medical device such as an implantable neural stimulation device or an integrated cardiac and neural stimulation device. Although implantable systems are illustrated and discussed, various aspects and embodiments of the present subject matter can be implemented in external devices. For example, neural signals can be sensed, and neural stimulation can be delivered, using implantable leads, external electrodes, percutaneous leads, or any combination of these.

Figure 13:
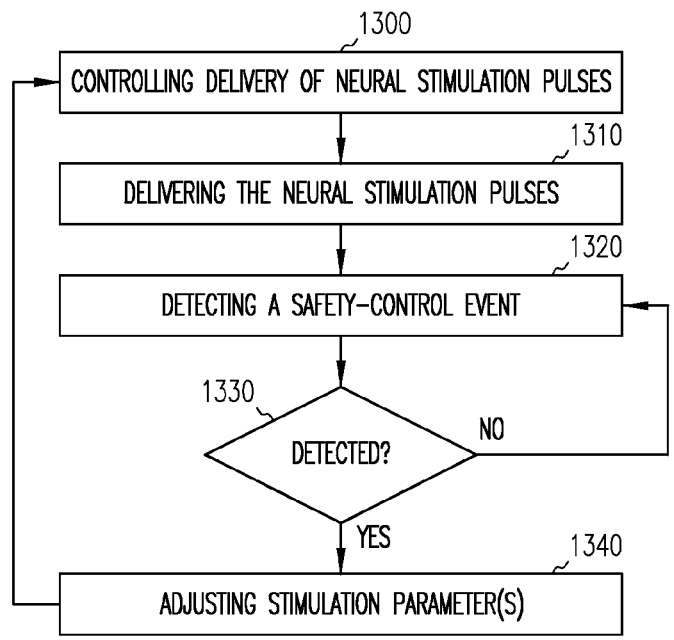
FIG. 13 is a flow chart illustrating an embodiment of a method for controlling safety of neural stimulation.

FIG. 13 is a flow chart illustrating an embodiment of a method for controlling safety of neural stimulation. In one embodiment, the method is performed by system 100, including the various embodiments discussed in this document.

Figure 14:
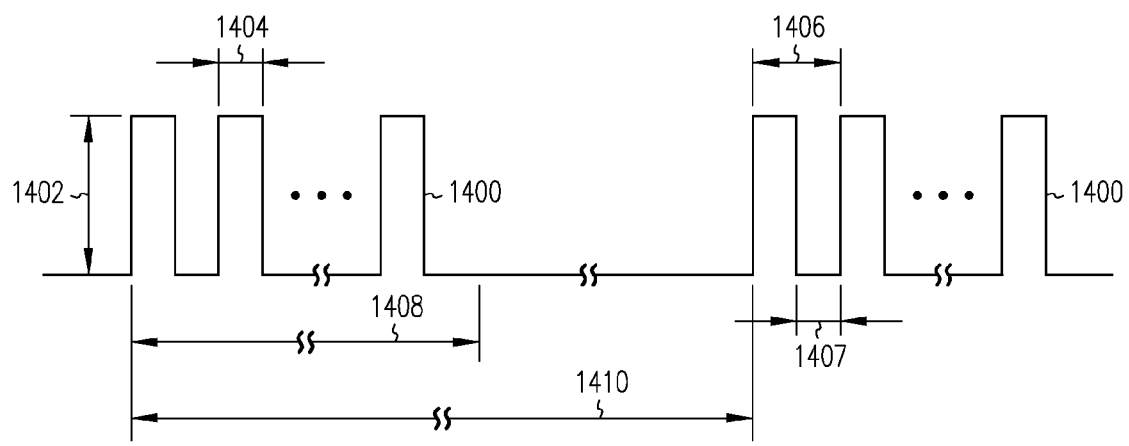
FIG. 14 is an illustration of an embodiment of a timing of neural stimulation pulses indicating stimulation parameters.

Delivery of neural stimulation pulses are controlled at 1300. The neural stimulation pulses are delivered through at least one electrode. The delivery of the neural stimulation pulses is controlled by using a plurality of stimulation parameters. In one embodiment, the delivery of the neural stimulation pulses through each electrode is controlled using stimulation parameters including pulse amplitude, pulse duration, and stimulation frequency. In a further embodiment, the neural stimulation pulses are delivered in bursts, and the stimulation parameters also include at least two of burst duration, burst interval, and stimulation duty cycle. FIG. 14 illustrates an embodiment of the timing of neural stimulation pulses 1400 showing these stimulation parameters. A pulse amplitude 1402 is the amplitude of a neural stimulation pulse. In a specific embodiment, stimulation output circuit 232 delivers constant-current neural stimulation pulses, and pulse amplitude 1402 is given as a current amplitude in milliampere (mA). A pulse width 1404 is the width of a neural stimulation pulse. In a specific embodiment, pulse width 1404 is given in milliseconds (ms) or microseconds (μs). A stimulation frequency is the frequency at which the neural stimulation pulses are delivered, given in Hertz (Hz) or pulses per second. Alternatively, the parameter controlling stimulation frequency is given as stimulation interval 1406 or inter-pulse interval 1407. Stimulation interval 1406 is the time interval between the beginnings of two successively delivered stimulation pulses, given in milliseconds (ms). Inter-pulse interval 1407 is the time interval between the end of a stimulation pulse and the beginning of the next stimulation pulse, given in milliseconds (ms). In one embodiment, bursts of the neural stimulation pulses are delivered. A burst duration 1408 is a time interval during which a burst of the neural stimulation pulses is delivered. In a specific embodiment, burst duration 1408 is given in milliseconds (ms), seconds (s), or minutes (min). A burst interval 1410 is the time interval between the beginnings of two successively delivered bursts of the neural stimulation pulses. In a specific embodiment, burst interval 1410 is given in milliseconds (ms) or seconds (s). Alternatively, the parameter controlling burst interval 1410 is the burst frequency in Hertz (Hz) or pulses per second, which is the frequency at which the delivery of a burst of the neural stimulation pulses is initiated. In another specific embodiment, the delivery of the bursts of the neural stimulation pulses is synchronized to cardiac cycles, and burst interval 1410 dynamically changes as a function of the heart rate or cardiac cycle length. The stimulation duty cycle is a ratio of burst duration 1408 to burst interval 1410. In a specific embodiment, the stimulation duty cycle is given as a percentage.

The neural stimulation pulses are delivered at 1310, according to the plurality of stimulation parameters. The neural stimulation pulses are delivered to one or more of the sympathetic and parasympathetic nervous systems regulating cardiac functions and hemodynamic performance.

A safety-control event is detected at 1320. The safety-control event is associated with values of the plurality of stimulation parameters. In one embodiment, a stimulation energy is detected at 1320. The stimulation energy is the total energy of the neural stimulation pulses delivered through an electrode over a predetermined period of time. The detection of the safety-control event is indicated at 1330 when the stimulation energy exceeds a predetermined threshold energy. In another embodiment, values of one or more stimulation parameters are detected at 1320. A detection of the safety-control event is indicated at 1330 when the value of at least one stimulation parameter exceeds a threshold value of that stimulation parameter. In a specific embodiment, the threshold value being a predetermined, fixed threshold value. In another specific embodiment, the threshold value is dynamically adjusted based on the value of at least another stimulation parameter. In another specification embodiment, the threshold value is determined by using a look-up table relating the threshold value to the value of at least another stimulation parameter. In one embodiment, one or more unintended effects associated with the delivery of the neural stimulation pulses are detected at 1320. A detection of the safety-control event is indicated at 1330 when one of the unintended effects is detected. In a specific embodiment, the value of a physiological parameter is sensed and compared to a normal value range. A detection of the unintended effect is indicated when the sensed value falls out of the normal value range. Examples of such a physiological parameter include heart rate, blood pressure, stroke volume, thoracic impedance, acceleration, acoustic parameter indicative coughing, and parameter related to an electromyogram. In another specific embodiment, a physiological signal indicative of the unintended effect is sensed, and the unintended effect is detected from that physiological signal. In another specific embodiment, a signal indicative of the detection of the unintended effect is received. In various specific embodiments, the detection of the safety-control events includes detection of one or more of cardiac arrhythmias, asystole, hypotension, infection, nerve paralysis, hypesthesia, facial paresis, vocal cord paralysis, facial paralysis, diaphragm paralysis, recurrent laryngeal nerve injury; urinary retention, low-grade fever, voice alteration, substantial increase in coughing, pharyngitis, paresthesia, dyspnea, apnea, hypopnea, dyspepsia, nausea, laryngismus, pain, and any other events known to be associated with electrical stimulation of the autonomic nervous system. In various embodiments, the detection of the safety-control events at 1320 includes detection of any one, or a combination of any two or more, of the stimulation energy, the one or more parameter values, and the one or more unintended effects.

If the safety-control event is detected at 1330, one or more stimulation parameters of the plurality of stimulation parameters are adjusted at 1340. In one embodiment, the value of a stimulation parameter is set to a threshold value of that stimulation parameter at 1340, when the value exceeds the threshold value. In one embodiment, one or more stimulation parameters are adjusted to reduce the intensity of the neural stimulation at 1340. In a specific embodiment, the intensity of the neural stimulation is reduced while the safety-control event is being detected. In another embodiment, one or more stimulation parameters are adjusted to suspend the delivery of the neural stimulation pulses at 1340. In a specific embodiment, the delivery of the neural stimulation pulses is suspended while the safety-control event is being detected.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of legal equivalents to which such claims are entitled.

What is claimed is:

1. A neural stimulation system, comprising:
   a stimulation output circuit configured to deliver neural stimulation pulses;
   a stimulation controller coupled to the stimulation output circuit, the stimulation controller configured to control the delivery of the neural stimulation pulses using stimulation parameters; and a safety controller coupled to the stimulation controller, the safety controller including:
    a safety-control event detection module including an energy detection module configured to detect a stimulation energy being an energy of one or more of the neural stimulation pulses and a stimulation parameter detection module configured to detect at least a first parameter value being a value of a first parameter of the stimulation parameters, the safety-control event detection module configured to indicate a detection of a safety-control event in response to the stimulation energy exceeding a threshold energy and indicate a detection of a safety-control event in response to the first parameter value exceeding a first threshold value; and
    a safety response module configured to adjust one or more parameters of the stimulation parameters in response to the detection of the safety-control event.

2. The neural stimulation system of claim 1, wherein the safety response module comprises a parameter limiting module configured to set the first parameter to the first threshold value in response to the first parameter value exceeding the first threshold value.

3. The neural stimulation system of claim 2, wherein the parameter limiting module is configured to adjust one or more parameters of the stimulation parameters to reduce an intensity of the neural stimulation pulses while the safety-control event is being detected.

4. The neural stimulation system of claim 1, wherein the safety response module comprises a stimulation switching module configured to suspend the delivery of the neural stimulation pulses in response to the detection of the safety-control event.

5. The neural stimulation system of claim 1, wherein the energy detection module is configured to detect the stimulation energy being an energy of one neural stimulation pulse of the neural stimulation pulses.

6. The neural stimulation system of claim 1, wherein the energy detection module is configured to detect the stimulation energy being a total energy of the neural stimulation pulses delivered over a specified period of time.

7. The neural stimulation system of claim 1, wherein the safety-control event detection module further comprises an unintended effect detection module configured to detect unintended effects associated with the delivery of the neural stimulation pulses.

8. The neural stimulation system of claim 7, wherein the unintended effect detector is configured to receive a signal indicative of the detection of the unintended effect.

9. The neural stimulation system of claim 7, wherein the unintended effect detector is configured to sense a signal indicative of the unintended effect and detect the unintended effect from that signal.

10. The neural stimulation system of claim 1, further comprising an implantable housing containing a neural stimulation circuit including the stimulation output circuit, the stimulation controller, and the safety controller.

11. A method for neural stimulation, comprising:
    delivering neural stimulation pulses;
    controlling the delivery of the neural stimulation pulses using stimulation parameters;
    detecting a safety-control event, including detecting a stimulation energy being an energy of one or more neural stimulation pulses of the neural stimulation pulses and detecting at least a first parameter value being a value of a first parameter of the stimulation parameters;
    indicating a detection of the safety-control event in response to the stimulation energy exceeding a threshold energy;
    indicating a detection of the safety-control event in response) the first parameter value exceeding a first threshold value; and
    adjusting one or more parameters of the stimulation parameters in response to the detection of the safety-control event.

12. The method of claim 11, wherein adjusting the one or more parameters comprises setting the first parameter to the first threshold value in response to the first parameter value exceeding the first threshold value.

13. The method of claim 11, wherein adjusting the one or more parameters comprises adjusting the one or more parameters to reduce an intensity of the neural stimulation pulses in response to the detection of the safety-control event while detecting the safety-control event.

14. The method of claim 11, wherein adjusting the one or more parameters comprises adjusting the one or more parameters such that the delivery of the neural stimulation pulses is suspended in response to the detection of the safety-control event.

15. The method of claim 11, wherein detecting the stimulation energy comprises detecting an energy of each pulse of the neural stimulation pulses.

16. The method of claim 11, wherein detecting the stimulation energy comprises detecting a total energy of the neural stimulation pulses delivered over a specified period of time.

17. The method of claim 11, wherein adjusting the one or more parameters of the stimulation parameters in response to the detection of the safety-control event comprises adjusting one or more of:
    a pulse amplitude being an amplitude of a pulse of the neural stimulation pulses; or
    a pulse width being a width of a pulse of the neural stimulation pulses.

18. The method of claim 11, wherein delivering neural stimulation pulses comprises delivering bursts of pulses of the neural stimulation pulses, and adjusting the one or more parameters of the stimulation parameters in response to the detection of the safety-control event comprises adjusting a stimulation frequency being a frequency at which the neural stimulation pulses are delivered during the delivery of a burst of the bursts of pulses.

19. The method of claim 11, wherein delivering neural stimulation pulses comprises delivering bursts of pulses of the neural stimulation pulses, and adjusting the one or more parameters of the stimulation parameters in response to the detection of the safety-control event comprises adjusting one or more of:
    a burst duration during which one burst of the bursts of pulses is delivered;
    a burst interval at which the bursts of pulses are delivered; or
    a stimulation duty cycle being a ratio of the burst duration to the burst interval.

20. The method of claim 11, wherein detecting the safety-control event further comprises detecting one or more unintended effects associated with the delivery of the neural stimulation pulses.

* * * * *